United States Patent
Sandler et al.

(10) Patent No.: US 8,636,929 B2
(45) Date of Patent: *Jan. 28, 2014

(54) NANOPOROUS FOAMED ACTIVE COMPOUND-CONTAINING PREPARATIONS BASED ON PHARMACEUTICALLY ACCEPTABLE THERMOPLASTICALLY WORKABLE POLYMERS

(75) Inventors: Jan Kurt Walter Sandler, Heidelberg (DE); Ingo Bellin, Mannheim (DE); Dejan Djuric, Mannheim (DE); Karl Kolter, Limburgerhof (DE); Holger Ruckdäschel, St. Martin (DE)

(73) Assignee: Basf SE, Ludwigshafen (DE)

( * ) Notice: Subject to any disclaimer, the term of this patent is extended or adjusted under 35 U.S.C. 154(b) by 58 days.

This patent is subject to a terminal disclaimer.

(21) Appl. No.: 13/111,999

(22) Filed: May 20, 2011

(65) Prior Publication Data
US 2011/0287066 A1 Nov. 24, 2011

Related U.S. Application Data

(60) Provisional application No. 61/346,924, filed on May 21, 2010.

(51) Int. Cl.
*B29C 67/20* (2006.01)
(52) U.S. Cl.
USPC .................. 264/41; 264/51; 264/140; 264/28
(58) Field of Classification Search
USPC ........................................ 264/41, 51, 140, 28
See application file for complete search history.

(56) References Cited

U.S. PATENT DOCUMENTS

| 4,041,115 A | * | 8/1977 | Jenkins et al. ..................... 264/5 |
| 4,853,420 A | * | 8/1989 | Pham et al. .................. 521/50.5 |

(Continued)

FOREIGN PATENT DOCUMENTS

| DE | 19635676 | 3/1998 |
| EP | 0932393 | 8/1999 |

(Continued)

OTHER PUBLICATIONS

Fujimoto, Youhei et al., "Well-Controlled Biodegradable Nanocomposite Foams: From Microcellular to Nanocellular", *Macromol. Rapid Commun.* 24 2003, 457-461.

(Continued)

*Primary Examiner* — Christina Johnson
*Assistant Examiner* — Saeed Huda
(74) *Attorney, Agent, or Firm* — Servilla Whitney LLC (57) ABSTRACT

Process for the production of nanoporous foamed active substance-containing preparations, wherein the active substance is present embedded in a pharmaceutically acceptable polymer, wherein, in stage a) loading of a polymeric molding composition or a polymer melt with a propellant is effected at a pressure and at a temperature at which the propellant is in the supercritical state, in stage b) heating of the laden polymer molding compound or melt is carried out under pressure at a temperature which lies in the range from −40 to +60° C., preferably −20 to +55° C., and especially preferably 0 to +50° C. around the glass transition temperature of the unladen (prior to loading) polymeric molding compound and in stage c) a depressurization of the polymeric molding compound or melt laden in stage a) and heated under pressure in stage b) is effected out with a depressurization rate in the range from 15,000 to 200,000 MPa/sec.

13 Claims, 2 Drawing Sheets

(56) References Cited

U.S. PATENT DOCUMENTS

| | | | |
|---|---|---|---|
| 5,000,991 A * | 3/1991 | Hayashi et al. | 428/36.5 |
| 5,158,986 A * | 10/1992 | Cha et al. | 521/82 |
| 5,670,102 A * | 9/1997 | Perman et al. | 264/50 |
| 5,830,923 A * | 11/1998 | Venkataraman | 521/64 |
| 5,912,278 A * | 6/1999 | Venkataraman | 521/145 |
| 5,955,511 A * | 9/1999 | Handa et al. | 521/97 |
| 6,005,013 A * | 12/1999 | Suh et al. | 521/79 |
| 6,150,424 A | 11/2000 | Breitenbach et al. | |
| 6,328,916 B1 * | 12/2001 | Nishikawa et al. | 264/53 |
| 6,503,427 B1 * | 1/2003 | Yamamoto et al. | 264/51 |
| 6,790,870 B1 * | 9/2004 | DeSimone et al. | 521/79 |
| 7,166,247 B2 * | 1/2007 | Kramer | 264/50 |
| 2007/0098801 A1* | 5/2007 | Verreck et al. | 424/489 |
| 2008/0293828 A1* | 11/2008 | Bouillo et al. | 514/772.3 |
| 2009/0130420 A1* | 5/2009 | Thiagarajan et al. | 428/221 |
| 2009/0148665 A1 | 6/2009 | Thiagarajan et al. | |
| 2010/0204425 A1* | 8/2010 | Mertoglu et al. | 526/264 |
| 2011/0178183 A1 | 7/2011 | Meyer-Boehm et al. | |
| 2011/0195118 A1 | 8/2011 | Kolter et al. | |
| 2011/0268972 A1 | 11/2011 | Schips et al. | |
| 2011/0269858 A1 | 11/2011 | Schips et al. | |
| 2011/0316198 A1 | 12/2011 | Schips et al. | |
| 2012/0022079 A1 | 1/2012 | Meyer-Böehm et al. | |
| 2012/0053248 A1 | 3/2012 | Kolter et al. | |
| 2012/0076858 A1 | 3/2012 | Kolter et al. | |
| 2012/0087823 A1 | 4/2012 | Joshi et al. | |

FOREIGN PATENT DOCUMENTS

| | | |
|---|---|---|
| EP | 1424124 | 6/2004 |
| WO | WO-98/09616 | 3/1998 |
| WO | WO-2005/023215 | 3/2005 |
| WO | WO-2007/051743 | 5/2007 |
| WO | WO-2008/087559 | 7/2008 |
| WO | WO-2009/013202 | 1/2009 |
| WO | WO-2010/012702 | 2/2010 |
| WO | WO-2010/034688 | 4/2010 |
| WO | WO-2010/040686 | 4/2010 |
| WO | WO-2010/066771 | 6/2010 |
| WO | WO-2010/076184 | 7/2010 |
| WO | WO-2010/076185 | 7/2010 |
| WO | WO-2010/076213 | 7/2010 |
| WO | WO-2010/100101 | 9/2010 |
| WO | WO-2010/112489 | 10/2010 |
| WO | WO-2010/130728 | 11/2010 |
| WO | WO-2010/139654 | 12/2010 |
| WO | WO-2010/139686 | 12/2010 |
| WO | WO-2011/026977 | 3/2011 |
| WO | WO-2011/026978 | 3/2011 |
| WO | WO-2011/026979 | 3/2011 |
| WO | WO-2011/029901 | 3/2011 |
| WO | WO-2011/032860 | 3/2011 |
| WO | WO-2011/032907 | 3/2011 |
| WO | WO-2011/032916 | 3/2011 |
| WO | WO-2011/033085 | 3/2011 |
| WO | WO-2011/086030 | 7/2011 |
| WO | WO-2011/144727 | 11/2011 |
| WO | WO-2011/144728 | 11/2011 |

OTHER PUBLICATIONS

Lee, Minhee et al., "Extrusion of PE/PS Blends with Supercritical Carbon Dioxide", *Polymer Engineering and Science*, vol. 38, No. 7 Jul. 1998, 1112-1120.

Lee, Lai Y. et al., "Paclitaxel release from micro-porous PLGA disks", *Chemical Engineering Science 64* 2009, 4341-4349.

* cited by examiner

NANOPOROUS FOAMED ACTIVE COMPOUND-CONTAINING PREPARATIONS BASED ON PHARMACEUTICALLY ACCEPTABLE THERMOPLASTICALLY WORKABLE POLYMERS

CROSS REFERENCE TO RELATED APPLICATIONS

This application claims the benefit of U.S. Provisional Application Ser. No. 61/346,924, filed May 21, 2010, the entire content of which is incorporated herein by reference.

BACKGROUND

The present invention relates to solid, nanoporous, foamed active compound-containing preparations based on pharmaceutically acceptable thermoplastically workable polymers. Further, the invention relates to processes for the production of such preparations.

It is generally known that foamed plastics can be produced by extrusion of melts containing volatile propellants.

Thus, in Polymer Engineering and Science, Vol. 38, No. 7, 1998, M. Lee et al. describe the extrusion of foamed polyethylene/polystyrene blends with supercritical carbon dioxide.

Particularly in the thermal insulation field, foams are used as insulating material. Since the mean free path of air is about 60 to 100 nanometers (depending on pressure and temperature), it can be concluded from this that in a polymer foam with air as the cell gas at an average cell size of less than or equal to 60 to 100 nanometers the contribution of the cell gas to the total thermal conduction of the foam is significantly reduced or even completely eliminated. Hence foams with as small-celled a structure as possible are especially desirable.

However it must be noted not only that the attainment of such a small cell size is important, but also that the foam density must be reduced as far as possible, in order not to lose the advantage gained via the cell gas through an increased contribution of the polymer matrix to the total thermal conduction. This means that a nanoporous foam must also have as low a density as possible in order to have an improved thermal insulating action compared to standard polymer foams.

In addition there is the problem that very small cell sizes can indeed often be present directly after the foaming, but then a maturation takes place with the formation of larger cells.

For example, in U.S. Pat. No. 5,955,511 and in EP1424124, processes for the production of micro- and nanoporous polymer foams are described, in which in a first step a polymer is loaded with a propellant under pressure at low temperatures below the glass transition temperature of the polymer. After depressurization without foaming, this laden polymer is then foamed in a separate step by increasing the temperature.

In WO2008/087559, continuous extrusion processes for the production of nanoporous polymer foams are described, in which a polymer is admittedly exposed to the propellant at different temperatures under pressure, but the subsequent foaming process by depressurization is performed at very low temperatures far below the glass transition temperature of the pure polymer but above the glass transition temperature of the gas-laden system.

In US2009/0130420, a continuous extrusion process for the production of nanoporous polymer foams is described, in which a polymer melt is loaded with propellant under pressure and is foamed by subsequent depressurization likewise in the region of the glass transition temperature of the gas-laden melt. Admittedly, high process pressures up to 1000 MPa are stated here for the loading, however the stated depressurization rate of 10 to 1000 MPa/s in combination with the low temperatures once again leads to a comparatively high foam density.

But foams are also of interest for pharmaceutical applications.

From EP-A 0 932 393 the production of solid foamed drug forms by extrusion and foaming of active compound-containing polymer melts containing active compounds and thermoplastic polymers such as homo- and copolymers of N-vinylpyrrolidone is known. These foamed drug forms are said to display markedly improved release of the active compound compared to the unfoamed extrudates.

From WO 2007/051743, the use of water-soluble or water-dispersible copolymers of N-vinyllactam, vinyl acetate and polyethers as solubilizers for pharmaceutical, cosmetic, food industry, agrotechical or other industrial applications is known. It is quite generally stated therein that the corresponding graft polymers can also be treated in the melt with the active compounds.

From WO 2009/013202 it is known that such graft polymers of N-vinyllactam, vinyl acetate and polyethers can be melted in the extruder and mixed with powder or liquid active compounds, and the extrusion at temperatures markedly below the melting point of the active compound is described.

From WO 2005/023215, flake-shaped foamed particles are known, which are produced by loading of an active compound-containing polymer melt with a supercritical propellant and expansion of the mixture. As polymers, copolymers of N-vinylpyrrolidone and vinyl acetate and an acrylate polymer (Eudragit E100 PO) are described. The foamed flake-shaped particles are said to enable more rapid release of the active compound in the aqueous medium.

However, not only are there process technology disadvantages with the processes described, but the product properties also reveal a need for further optimization.

The systems produced are often microporous or macroporous and also inhomogeneous. Here "microporous" means that the pore sizes lie in the range from 1 to 1000 micrometers. The term "macroporous" designates dimensions greater than 1000 micrometers.

The mechanical properties of the foams which are not insignificant for the further processing to administration forms also reveal a need for further optimization.

SUMMARY

Hence, embodiments of the present invention provide processes for the production of nanoporous foamed polymers with improved application technology properties, whereby by means of the process according to embodiments of the invention both open- and also closed-cell foam morphologies with cell sizes in the nanometer range, but preferably open-celled systems, are to be created. Further, deliberate adjustment of the cell size and the foam density should be possible with high and designated precision and the processes should be simpler to perform compared to the known processes.

The problem is solved according to embodiments of the invention in that the process for the production of nanoporous foamed preparations of low foam density is divided into at least 3 steps, which however are all effected directly one after another without removal of the polymeric molding compound until the depressurization step.

According to this, nanoporous foamed active compound-containing preparations were found, in which the active compounds are present embedded in at least one thermoplastically workable pharmaceutically acceptable polymer.

Further, a process for the production of the preparations is provided wherein there are effected in stage a) loading of a polymeric molding compound or of a polymer melt containing at least one pharmaceutically acceptable polymer with a propellant under a pressure and at a temperature at which the propellant is in the supercritical state, in stage b) heating of the polymer molding compound or polymer melt laden in stage a) under pressure at a temperature which lies in the range from −40 to +60° C. below or above the glass transition temperature of the polymeric molding compound prior to loading or the mixture of polymer and active compound prior to loading, and in stage c) depressurization of the polymer molding compound or polymer melt laden in stage a), which contains at least one active compound, with a depressurization rate in the range from 15,000 to 2,000,000 MPa/s.

Optionally a stage d) may follow, in which the nanoporously foamed preparations obtained are comminuted.

Preferably the laden polymer molding compound or polymer melt is heated such that the temperature at the instant of foaming lies in the range from −40 to +55° C. around the glass transition temperature of the non-gas-laden polymer compound. Especially preferable is a temperature range which deviates by about 0 to +40° C. from the glass transition temperature of the mixture of polymer and active compound.

The determinable glass transition temperature is described as the glass transition temperature. The glass transition temperature can be determined by means of DSC according to DIN-ISO 11357-2 at a heating rate of 20 K/min.

The addition of one or more active compounds can be effected at different times. According to one embodiment, active compound and polymer component can be mixed before melting. The addition of the active compound can also be effected in stage b). With particularly temperature-sensitive active compounds, the addition to the melt after the admixture of propellant and heating have taken place, i.e. between stage b) and stage c), is advisable.

DETAILED DESCRIPTION

By means of the process according to embodiments of the invention, nanoporous active compound-containing polymer foams with an average cell count in the range from 1,000 to 100,000 cells/mm, preferably from 2,000 to 50,000 and especially preferably from 5,000 to 50,000 cells/mm, and a foam density in the range from 10 to 700 kg/m$^3$, preferably in the range from 10 to 300 kg/m$^3$, especially preferably in the range from 10 to 500 kg/m$^3$, are produced.

According to embodiments of the invention, the term "nanoporous" comprises average cell sizes in the range from 10 to 1000 nanometers, preferably from 20 to 500 nm and especially preferably from 20 to 200 nm.

According to embodiments of the invention, the term "average cell size" describes the average diameter of spherical foam cells with cross-sectional areas equivalent to the real cells in typical frequency/size curves, such as can be determined from evaluation of at least 10 real cell areas from representative electron micrographs.

According to embodiments of the invention, the term "foam density" or also "density" describes the mass to volume ratio of the foamed nanoporous molding compound, which can be determined by the buoyancy method or is obtained by calculation from the mass to volume quotient of a molded part.

According to embodiments of the invention, the term "molding compound" or also "melt" includes both pure homo- and also copolymers and mixtures of polymers. Furthermore, the term also includes formulations, which are based on polymers and a great diversity of additives. For example, mention may be made here merely of process additives such as for example stabilizers, flow aids, color additives, antioxidants and similar additives well known to those skilled in the art.

The foams can be closed-cell, but are preferably open-cell. "Closed-cell" means that a discontinuous gas phase and a continuous polymer phase are present.

"Open-cell" means that there is a bicontinuous system, in which the gas phase and the polymer phase are each continuous phases, the two phases being interpenetrating phases.

The nanoporous systems have an open cell content of more than 40%, preferably more than 50%, especially preferably more than 75%. In the ideal case, at least 90% of the cells, up to 100% of the cells, are open, i.e. the foam consists only of webs. The open cell content can be determined according to DIN-ISO 4590.

In the first stage, a polymeric molding compound or a melt is loaded with a gas or a fluid as propellant under a pressure and at a temperature at which the propellant is in the supercritical state.

As volatile, physiologically acceptable propellants, gaseous propellants such as carbon dioxide, nitrogen, air, noble gases such as for example helium or argon, and also ethane, propane, butane, n-pentane, volatile aliphatic alcohols such as ethanol or isopropanol, chlorofluorohydrocarbons, difluoroethane, trifluoromethane, dimethyl ether or dinitrogen oxide (laughing gas) are suitable, carbon dioxide, laughing gas and/or nitrogen being preferable. Quite especially preferable is carbon dioxide. The conditions under which these propellants are in the supercritical state are well known to those skilled in the art.

According to embodiments of the invention, this means that the propellant can be dispensed and/or injected directly supercritically, or the process parameters of the polymer to be injected at the time of the injection lie in a range such that the propellant becomes supercritical under these conditions. For $CO_2$, for example, the critical point lies in the region of 31° C. and 7.375 MPa, for $N_2O$ for example the critical point lies in the region of 36.4° C. and 7.245 MPa.

The propellant loading of the polymeric molding compound or polymer melt can according to embodiments of the invention be effected in a pressure chamber, e.g. an autoclave, or in a tool cavity or in an extruder. According to embodiments of the invention, the exact temperature of the polymer molding compound in this stage is unimportant, although a temperature over the critical temperature of the propellant and above the glass transition temperature of the polymeric molding compound is advantageous for this first loading step, since the uptake of the propellant via diffusion processes is accelerated at temperatures above the glass transition temperature of the polymeric molding compound and hence shorter loading times are possible.

According to embodiments of the invention, for the loading a pressure above the critical pressure of the propellant, preferably greater than 10 MPa, especially preferably greater than 20 MPa, is set. This loading pressure is important for the generation of as high as possible a gas concentration in the polymeric molding compound or the polymer melt, and in the context of the technical possibilities of present-day pressure vessels can be set at up to 200 MPa.

According to one embodiment of the invention, the loading is effected in an extruder. In an advantageously configured version, the temperature of the polymeric molding compound in the region of the propellant injection is above the glass transition temperature of the molding compound, so that the propellant can distribute and dissolve very well and rapidly in the polymer melt. The loading pressure during this is generally set higher than the melt pressure in this region. In an especially advantageous implementation, the loading pressure is set at a constant high value via a pressure maintaining valve. Thereby, according to embodiments of the invention, a propellant mass flow is set which can amount to 1 to 50 wt. % based on the mass flow of the polymeric molding compound. The upper limit here is the saturation concentration attainable with the parameters pressure and temperature of the laden melt before the nozzle, which can either be determined empirically in the process, or by gravimetric methods.

In a second stage of the processes according to embodiments of the invention, while maintaining the loading pressure greater than 10 MPa, preferably greater than 20 MPa, the laden polymeric molding compound or polymer melt is now cooled to a temperature which lies in the range from 40° C. below to 55° C. above the glass transition temperature (Tg) of the mixture of polymer and active compound determinable by DSC according to DIN-ISO 11357-2 at a heating rate of 20 K/min, preferably in the range from 20° C. below to +50° C. above the Tg, especially preferably in the range from 0° C. below to 40° C. above the Tg.

According to one embodiment of the process according to embodiments of the invention, in which the loading is effected in the autoclave, this adjustment of the temperature of the polymeric molding compound can be effected after application of the loading pressure. Alternatively, this temperature can also already be set before application of the loading pressure. In both process versions, care must be taken to allow sufficient time for homogenization of the temperature, in particular after injection of the cold propellant into the cavity. Furthermore, in these process versions, care must be taken to allow sufficient time for attainment of the saturation concentration by diffusion, in particular at high volumes of the polymeric molding compound.

According to a further embodiment of the invention, the loading is effected in an extruder, during which the laden molding compound or polymer melt is continuously cooled. For this, all equipment known to the person skilled in the art, from a cooling extruder up to mixers and coolers, can be used in any number and combination. In order to maintain the pressure in the laden molding compound, the use of melt pumps to increase the pressure, which can also be used in any number and position in the process, can be appropriate. An advantage of one embodiment of the invention is also based on this in that in fact a segmental build-up of the process line offers great control over the local parameters pressure and temperature and rapid and homogeneous cooling of the laden molding compound under pressure can be effected. A precondition is however that through a sufficient residence time and thorough mixing a homogeneous distribution of the propellant molecules is effected and the propellant can be completely dissolved in the polymeric molding compound.

Surprisingly, experimental studies have shown that, contrary to general expert opinion, a rapid depressurization of a polymeric molding compound or polymer melt laden and heated according to embodiments of the invention leads in the third stage (stage c)) to stable nanoporous polymer foams of low density.

By setting a depressurization rate in the range from 15,000 to 2,000,000 MPa/s, a polymeric molding compound with very high propellant concentration and correspondingly low viscosity can be produced even with homogeneous foam temperatures above the glass transition temperature of the non-gas-laden molding compound to give a nanoporous foam morphology with at the same time markedly lower foam density. According to one preferred embodiment of the invention, depressurization rates are set of from 30,000 to 1,000,000 MPa/s, more preferably 40,000 to 500,000 MPa/s.

According to a further embodiment of the invention, depressurization rates of 15,000 to 200,000 MPa/s may also be sufficient.

In a third stage (stage c)), as stated, there is a depressurization of the polymer melt laden with propellant in stage a) and heated in stage b), at a depressurization rate in the range from 15,000 to 2,000,000 MPa/sec.

The depressurization rate relates to the pressure jump which takes place within a period of one second prior to foaming. The pressure drop in this context is at least 10 MPa.

The pressure prior to depressurization may be determined by means of a pressure sensor. Depressurization takes place typically to atmospheric pressure. It is also possible, though, to apply a slight overpressure or underpressure. Generally speaking, the pressure drop takes place in a jump, within from 0.1 to 10 ms. The depressurization rate may be determined, for example, by placing a tangent in the region of the greatest pressure drop in the pressure/travel diagram.

In the continuous embodiment by means of an extruder, the depressurization rate is typically set via the shape of the die. Generally speaking, for this purpose, a die is used which has at least one die section with, preferably, lengths from 1 to 5 mm and a cross section of 0.1-25 $mm^2$.

According to embodiments of the invention, this third stage can be effected in different ways in different process versions. In a version in the autoclave, the depressurization rate according to embodiments of the invention can if desired be ensured via rapidly switching valves or via the controlled operation of depressurization devices such as for example a bursting disk. In a version according to embodiments of the invention in which the process is carried out in a tool cavity, the depressurization rate can be set by rapid expansion of the cavity.

In the preferred implementation according to embodiments of the invention in an extruder, the depressurization rate is ensured by the output capacity of the extruder and the nozzle geometry.

The present invention further relates to other equipment and methods familiar to the expert person skilled in the art technically usable for the production of such nanoporous polymer foams by the aforesaid rapid depressurization according to embodiments of the invention of a polymeric molding compound heated according to embodiments of the invention.

Depending on the nozzle geometry used, particularly in the extrusion process, foam structures and finally polymer foams of various shapes can be produced. In preferred implementations of the process according to embodiments of the invention, solid profiles or hollow profiles are produced. In an also preferred configuration of the process according to embodiments of the invention, in a further process step the polymer foam is comminuted into molded bodies in the form of foamed polymer particles, granules or powders, e.g. by means of a cutting disk, a granulator, a blade, a fly cutter or a mill. The comminution step here can preferably be included directly after the depressurization, but can also be performed at a later time. During this, it can be advantageous to cool the polymer foam, for example by means of ice-water, dry ice or liquid nitrogen.

As thermoplastically workable polymers for the polymer matrix, according to embodiments of the invention amorphous, thermoplastic polymers are possible. All pharmaceutically acceptable polymers are suitable. Preferably, water-soluble or water-dispersible polymers are used. It can however also be advisable to mix the water-soluble or water-dispersible polymers with polymers poorly soluble in water.

According to one embodiment of the invention, amphiphilic copolymers are especially suitable as matrix material for the foamed molding compounds. As amphiphilic copolymers, polyether-containing graft polymers above all are suitable. These are obtained by radical polymerization of vinyl monomers in the presence of a polyether component, which serves as the graft base.

Particularly suitable for the production of the foamed preparations are polyether graft polymers which are obtained by radical initiated polymerization of a mixture of i) 30 to 80 wt. % N-vinyllactam, ii) 10 to 50 wt. % vinyl acetate and iii) 10 to 50 wt. % of a polyether, with the proviso that the sum of i), ii) and iii) is equal to 100 wt. %.

The polyether copolymers are readily soluble in water, which means that at 20° C. 1 part of copolymer dissolves in 1 to 10 parts of water.

According to one embodiment of the invention, preferred polyether copolymers obtained from:
i) 30 to 70 wt. % N-vinyllactam
ii) 15 to 35 wt. % vinyl acetate, and
iii) 10 to 35 wt. % of a polyether, are used.

Especially preferably used polyether copolymers are obtainable from:
i) 40 to 60 wt. % N-vinyllactam
ii) 15 to 35 wt. % vinyl acetate
iii) 10 to 30 wt. % of a polyether Quite especially preferably used polyether copolymers are obtainable from
i) 50 to 60 wt. % N-vinyllactam
ii) 25 to 35 wt. % vinyl acetate, and
iii) 10 to 20 wt. % of a polyether.

The proviso that the sum of the components i), ii), and iii) is equal to 100 wt. % also applies for the preferred and especially preferred compositions.

As the N-vinyllactam, N-vinylcaprolactam or N-vinylpyrrolidone or mixtures thereof are possible. Preferably, N-vinylcaprolactam is used.

Polyethers are used as the graft base. As possible polyethers, polyalkylene glycols are preferable. The polyalkylene glycols can have molecular weights of 1000 to 100000 D [Dalton], preferably 1500 to 35000 D, especially preferably 1500 to 10000 D. The molecular weights are determined from the OH number measured according to DIN 53240.

As possible polyalkylene glycols, polyethylene glycols are especially preferable. Further, polypropylene glycols, polytetrahydrofurans or polybutylene glycols, which are obtained from 2-ethyloxirane or 2,3-dimethyloxirane, are also suitable.

Random or block copolymers of polyalkylene glycols obtained from ethylene oxide, propylene oxide and butylene oxides such as for example polyethylene glycol-polypropylene glycol block copolymers are also suitable polyethers. The block copolymers can be of the AB or the ABA type.

The preferable polyalkylene glycols also include those which are alkylated at one or both OH terminal groups. Possible alkyl residues are branched or unbranched $C_1$ to $C_{22}$ alkyl residues, preferably $C_1$-$C_{18}$ alkyl residues, for example methyl, ethyl, n-butyl, isobutyl, pentyl, hexyl, octyl, nonyl, decyl, dodecyl, tridecyl or octadecyl residues.

General processes for the production of the polyether copolymers according to embodiments of the invention are known per se. They are produced by radical initiated polymerization, preferably in solution, in non-aqueous, organic solvents or in mixed non-aqueous/aqueous solvents. Suitable production processes are for example described in WO 2007/051743 and WO 2009/013202, to the disclosure whereof concerning the production process reference is expressly made.

Preferably suitable as an amphiphilic copolymer is a copolymer commercially available under the brand name Soluplus®, BASF SE.

Further, graft polymers which consist of polyethers as the graft base and polyvinyl alcohol units grafted thereon are also suitable.

Also suitable as polymers are for example water-soluble, thermoplastically workable homopolymers or random copolymers of N-vinylpyrrolidone or mixtures of such polymers. The polymers normally have glass transition temperatures in the range from 80 to 190, preferably 90 to 175° C. Suitable homopolymers are for example polymers with Fikentscher K values in the range from 10 to 30. Suitable copolymers can contain as comonomers unsaturated carboxylic acids, e.g. methacrylic acid, crotonic acid, maleic acid, itaconic acid, and esters thereof with alcohols with 1 to 12, preferably 1 to 8 carbon atoms, hydroxyethyl or hydroxypropyl acrylate and methacrylate, (meth)acrylamide, the anhydrides and half esters of maleic acid and itaconic acid (where the half ester is preferably only formed after the polymerization), or vinyl monomers such as N-vinylcaprolactam, vinyl acetate, vinyl butyrate and vinyl propionate, or also mixtures of said comonomers. Thus for example terpolymers of N-vinylpyrrolidone, vinyl acetate and vinyl propionate are suitable.

Preferred comonomers are acrylic acid and, especially preferably, vinyl acetate. The comonomers can be contained in proportions from 20 up to 70 wt. %. Quite especially preferable are copolymers according to embodiments of the invention which are obtained from 60 wt. % N-vinylpyrrolidone and 40 wt. % vinyl acetate.

Also suitable polymers are for example homo or copolymers of vinyl chloride, polyvinyl alcohols, polystyrene, polyhydroxybutyrates or copolymers of ethylene and vinyl acetate.

Further, water-soluble or water-dispersible block copolymers, for example those with vinyllactam blocks, are also suitable.

As stated, the polymer matrix can also contain polymers poorly soluble in water. In the sense of the invention, polymers poorly soluble in water should be understood to mean either neutral poorly soluble polymers (retard polymers), anionic poorly soluble polymers (gastric juice-resistant polymers) or basic poorly soluble polymers.

Poorly soluble polymers are understood to mean polymers which are poorly water-soluble or only swellable in water over the whole pH range from 1 to 14. As a rule, only one water-insoluble polymer is contained in the pharmaceutical composition. However, two or more water-insoluble polymers can optionally be present jointly or mixed.

Suitable Poorly Soluble Polymers are for Example:
Neutral Poorly Soluble Polymers Neutral or essentially neutral methacrylate copolymers. These can in particular consist of at least 95, in particular at least 98, preferably at least 99, in particular at least 99, especially preferably 100 wt. %, of radical polymerized (meth)acrylate monomers with neutral residues, in particular C1 to C4 alkyl residues.

Suitable (meth)acrylate monomers with neutral residues are for example methyl methacrylate, ethyl methacrylate, butyl methacrylate, methyl acrylate, ethyl acrylate and butyl acrylate. Methyl methacrylate, ethyl acrylate and methyl acrylate are preferred.

In small proportions, of less than 5, preferably at most 2, especially preferably at most 1 or 0.05 to 1 wt. %, methacrylate monomers with anionic residues, e.g. acrylic acid and/or methacrylic acid, can be contained.

Neutral or almost neutral (meth)acrylate copolymers of 20 to 40 wt. % ethyl acrylate, 60 to 80 wt. % methyl methacrylate and 0 to less than 5, preferably 0 to 2 or 0.05 to 1 wt. % (Eudragit® NE type) are for example suitable.

Eudragit NE is a copolymer of 30 wt. % ethyl acrylate and 70 wt. % methyl methacrylate.

Further suitable poorly soluble (meth)acrylate copolymers are for example polymers soluble or swellable independently of the pH, which are suitable for drug coatings.

The poorly soluble polymer can be a polymer of 98 to 85 wt. % C1 to C4 alkyl esters of acrylic or methacrylic acid and 2 to 15 wt. % (meth)acrylate monomers with a quaternary ammonium group or a mixture of several polymers of this substance class.

The poorly soluble polymer can also be a polymer of 97 to more than 93 wt. % C1 to C4 alkyl esters of acrylic or methacrylic acid and 3 to less than 7 wt. % (meth)acrylate monomers with a quaternary ammonium group (Eudragit® RS type).

Preferred C1 to C4 alkyl esters of acrylic or methacrylic acid are methyl acrylate, ethyl acrylate, butyl acrylate, butyl methacrylate and methyl methacrylate.

As a (meth)acrylate monomer with quaternary amino groups, 2-trimethylammonium-ethyl methacrylate chloride is especially preferred.

A suitable copolymer for example contains 65 wt. % methyl methacrylate, 30 wt. % ethyl acrylate and 5 wt. % 2-trimethylammonium-ethyl methacrylate chloride (Eudragit RS).

The poorly soluble polymer can be a polymer of 93 to 88 wt. % C1 to C4 alkyl esters of acrylic or methacrylic acid and 7 to 12 wt. % (meth)acrylate monomers with a quaternary ammonium group (Eudragit RL type).

A specific suitable copolymer for example contains 60 wt. % methyl methacrylate, 30 wt. % ethyl acrylate and 10 wt. % 2-trimethylammoniumethyl methacrylate chloride (Eudragit® RL).

The water-insoluble polymer can be a mixture of the polymers of the Eudragit RS type and the Eudragit RL type in the ratio of 20 to 1 to 1 to 20.

Also especially suitable are mixtures of Eudragit RS and Eudragit RL e.g. in the ratio of 20:1 to 1:20 parts by weight.

The pharmaceutical composition can also contain a polyvinyl acetate as a poorly soluble polymer. As polyvinyl acetates, for example the homopolymers of vinyl acetate are suitable. Furthermore, poorly soluble polyvinyl acetate copolymers, for example water-insoluble copolymers of vinyl acetate and N-vinylpyrrolidone are suitable. Suitable commercially available polyvinyl acetates are for example Kollicoat® SR 30D or Kollidon® SR.

As poorly soluble polymers, alkylcelluloses such as for example ethylcellulose are also suitable. Furthermore, hydroxypropylmethylcellulose acetate succinate and hydroxypropylmethylcellulose acetate phthalate are suitable.

Anionic Poorly Soluble Polymers

Furthermore, anionic poorly soluble polymers can also be used. Anionic polymers are understood to be preferably polymers with at least 5%, especially preferably 5 to 75%, monomer residues with anionic groups. Anionic (meth)acrylate copolymers are preferred.

Suitable commercially available (meth)acrylate copolymers with anionic groups are for example the Eudragit® types L, L100-55, S and FS.

Suitable anionic (meth)acrylate copolymers are e.g. polymers of 25 to 95 wt. % C1 to C4 alkyl esters of acrylic or methacrylic acid and 5 to 75 wt. % (meth)acrylate monomers with an anionic group. Depending on the content of anionic groups and the nature of the other monomers, corresponding polymers are water-soluble at pH values above pH 5.0 and hence are also gastric juice-soluble. As a rule, the stated proportions add up to 100 wt. %.

A (meth)acrylate monomer with an anionic group can for example be acrylic acid, but preferably methacrylic acid.

Also suitable are anionic (meth)acrylate copolymers of 40 to 60 wt. % methacrylic acid and 60 to 40 wt. % methyl methacrylate or 60 to 40 wt. % ethyl acrylate (Eudragit L or Eudragit L1 00-55 types).

Eudragit L is a copolymer of 50 wt. % methyl methacrylate and 50 wt. % methacrylic acid.

Eudragit L1 00-55 is a copolymer of 50 wt. % ethyl acrylate and 50 wt. % methacrylic acid. Eudragit L 30D-55 is a dispersion containing 30 wt. % Eudragit L 100-55.

Also suitable are anionic (meth)acrylate copolymers of 20 to 40 wt. % methacrylic acid and 80 to 60 wt. % methyl methacrylate (Eudragit® S type).

Also suitable are for example anionic (meth)acrylate copolymers consisting of 10 to 30 wt. %, methyl methacrylate, 50 to 70 wt. % methyl acrylate and 5 to 15 wt. % methacrylic acid (Eudragit® FS type).

Eudragit FS is a copolymer of 25 wt. % methyl methacrylate, 65 wt. % methyl acrylate and 10 wt. % methacrylic acid. Eudragit FS 30 D is a dispersion containing 30 wt. % Eudragit® FS.

The copolymers preferably consist essentially to exclusively of the monomers methacrylic acid, methyl acrylate and ethyl acrylate in the aforesaid weight proportions.

However, in addition, without this leading to impairment of the essential properties, small quantities in the range from 0 to 10, e.g. 1 to 5 wt. %, of other vinylically copolymerizable monomers such as for example methyl methacrylate, butyl methacrylate, butyl acrylate or hydroxyethyl methacrylate can also be contained.

The copolymers can be produced by common processes of radical polymerization continuously or discontinuously (batch processes) in the presence of radical-forming initiators and optionally regulators for adjustment of the molecular weight, in substance, in solution, by bead polymerization or in emulsion. The average molecular weight Mw (weight average, determined for example by measurement of the solution viscosity) can for example lie in the range from 80,000 to 1,000,000 (g/mol). Emulsion polymerization in the aqueous phase in the presence of water-soluble initiators and (preferably anionic) emulsifiers is preferred. In the case of substance polymerization the copolymer can be processed in solid form by crushing, extrusion, granulation or hot-chopping.

Basic Poorly Soluble Polymers

Basic polymers such as basic meth(acrylates) or chitosan can also be used. An example of an appropriate commercially available polymer is Eudragit® E or EPO, which is a copolymer of methyl methacrylate, butyl methacrylate and dimethylamino-ethyl methacrylate.

The nanoporous foamed active compound preparations according to embodiments of the invention can contain as active compounds all biologically active compounds which can be incorporated into the polymer melt undecomposed under the processing conditions.

Suitable Active Compounds are for Example:

Acebutolol, acetylcysteine, acetylsalicylic acid, acyclovir, alprazolam, albumin, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, azemetacin, beclomethasone, benscerazide, benzalkonium hydroxide, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidine, ceftriaxone, cefuroxime, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomibramine, clonazepam, clonidine, clotrimazole, clozapin, codeine, colestyramine, cromoglycic acid, cyanocobalamine, cyproterone, desogestrel, dexamethasone, dexpanthenol, dextromethorphan, dextropropoxiphene, diazepam, diclofenac, digoxin, dihydrocodeine, dihydroergotamine, dilthiazem, diphenhydramine, dipyridamole, dipyrone, disopyramide, domperidone, dopamine, doxocyclin, enalapril, enrofloxacin, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, flutamide, furosemide, gemfibrozil, gentamicin, Ginkgo biloba, glibenclamine, glipizide, Glycyrrhiza glabra, guaifenesin, haloperidol, heparin, hyaluronic acid, hydrochloro-thiazide, hydrocodone, hydrocortisone, hydromorphone, hydroxytetracycline, ipratropium hydroxide, ibuprofen, imipenem, indomethacin, iohexol, iopamidol, isosorbide dinitrate, isosorbide mononitrate, isotredinoin, kethotifen, ketoconazole, ketoprofen, ketorolac, labetalon, lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misobrostol, morphine, multivitamins and minerals, nystatin, N-methyl-ephedrine, naftidrofuril, naproxen, neomycin, nicardipine, nicergoline, nicotinamide, nicotine, nicotinic acid, nifedipine, nimodipine, nitrendipine, nizatidine, norethisterone, norfloxacin, norgestrel, nortriptyline, ofloxacin, omeprazole, ondansetron, pancreatin, panthenol, pantoprazol, pantothenic acid, paracetamol, penicillin G, penicillin V, phenobarbital, phenoxifylline, phenylephrine, phenylpropanolamine, phenytoim, piroxicam, polymyxin B, povidone-iodine, pravastatin, prazepam, prazosin, prednisolone, prednisone, proglumetacin, propafenone, propranolol, pseudoephedrine, pyridoxine, quinidine, ramipril, ranitidine, reserpine, retinol, riboflavin, rifampicin, rionavir, rutoside, saccharin, salbutamol, salcatonin, salicylic acid, sildenafil, simvastatin, somatropin, sotalol, spironolactone, sucralfate, sulbactam, sulfamethoxazole, sulpiride, tamoxifen, tegafur, tenoxicam, teprenone, terazosin, terbutaline, terfenadine, theophylline, thiamine, thiaprofenic acid, ticlopidine, timolol, tranexamic acid, tretinoin, triamcinolone, acetonide, triamterene, trimethoprim, troxerutin, uracil, valproic acid, vancomycin, verapamil, vitamin E, volinic acid, zidovudine and zotepin.

Vitamins can also be formulated according to embodiments of the invention. Among these are the vitamins of the A group, the B group, where, apart from B1, B2, B6 and B12 and nicotinic acid and nicotinamide, compounds with vitamin B properties, such as for example adenine, choline, pantothenic acid, biotin, adenylic acid, folic acid, orotic acid, pangamic acid, carnitine, p-aminobenzoic acid, myo-inositol and alpha-lipoic acid, are also understood thereby, and also vitamins of the C group, D group, E group, F group, H group, I and J group, K group and P group.

Plant protection agents, other biocides or veterinary medical substances are also possible as active compounds.

The preparations according to embodiments of the invention are preferably suitable for the incorporation of active compounds poorly soluble in water. The term "poorly soluble in water" is to be understood as follows according to embodiments of the invention: The term "poorly soluble in water" according to embodiments of the invention comprises poorly soluble to practically insoluble substances and means that for a solution in water at 20° C. of the substance to be dissolved, at least 100 g of water is needed per g of substance. With practically insoluble substances, at least 10,000 g of water is needed per g of substance.

Furthermore, the active compound preparations can also contain starches, degraded starches, casein, pectin, chitin, chitosan, gelatins or shellac as matrix components, which can be processed in the melt with the addition of normal plasticizers.

Furthermore, the preparations according to embodiments of the invention can contain the normal pharmaceutical additives such as fillers, lubricants, mold release agents, flow regulators, plasticizers, colorants and stabilizers in proportions up to 50 wt. %. These and the proportions stated below are each based on the total weight of the preparation (=100%).

As fillers, for example the oxides of magnesium, aluminum, silicon and titanium and lactose, mannitol, sorbitol, xylitol, pentaerythritol and its derivatives may be mentioned, with the content of filler lying in the range from 0.02 to 50, preferably 0.2 to 20 wt. %.

As flow regulators, for example the mono, di and triglycerides of the long-chain fatty acids such as C12, C14, C16- and C18 fatty acids, waxes such as Carnauba wax and the lecithins may be mentioned, with the content lying in the range from 0.1 to 30, preferably 0.1 to 5 wt. %.

As plasticizers, for example apart from low molecular weight polyalkylene oxides such as polyethylene glycol, polypropylene glycol and polyethylenepropylene glycol polyhydric alcohols such as propylene glycol, glycerin, pentaerythritol and sorbitol and sodium diethylsulfosuccinate, glycerin mono, di and triacetate and polyethylene glycol stearic acid esters may be mentioned. Here the content of plasticizer is ca. 0.5 to 15, preferably 0.5 to 5 wt. %.

As lubricants, for example stearates of aluminum or calcium and talc and silicones may be mentioned, with the content thereof lying in the range from 0.1 to 5, preferably 0.1 to 3 wt. %.

As stabilizers, for example light stabilizers, antioxidants, radical absorbers and stabilizers against microbial attack may be mentioned, with the content thereof preferably lying in the range from 0.01 to 0.05 wt. %.

In order to produce the preparations according to embodiments of the invention, the active compound component can either be mixed beforehand with the polymer and then extruded, or else can be metered in during the extrusion of the propellant-containing polymer melt.

The weight ratios of the individual components in the preparation are variable within wide limits. Depending on the effective dose and release rate of the active compound, the content thereof can be 0.1 to 90 wt. % of the active compound preparation. The content of the polymer can be 10 to 99.9 wt. %. In addition, 0 to 50 wt. % of one or more additives can be contained.

The foamed forms can also be provided with a normal active substance-permeable coating, so that floating buoyant forms can be simply obtained. Such buoyant forms can be used for pharmaceutical purposes or else for the veterinary medical or agrotechnical products, for example for the production of slow-sinking fish foods.

The solid, foamed active compound preparations obtained according to embodiments of the invention, which contain the active compound homogeneously dispersed in the polymer matrix, dissolve very rapidly and thus enable the rapid release of the active compound. Through the process according to embodiments of the invention, the foamed active compound preparations can be obtained simply and economically. It is also advantageous that owing to the viscosity-reducing action of the propellant it is possible to extrude at markedly lower temperatures than without propellant, so that the active compounds are less subjected to thermal stress.

In the preparations according to embodiments of the invention, the active compound is embedded in amorphous form. Amorphous means that not more than 3 wt. % of the active compound, measured by DSC, is present in crystalline form. The DSC measurement is effected at a heating rate of 20 K/min.

The foamed active compound preparation is then shaped into the particular desired active compound forms, for example by pelleting, granulation or tableting by known processes. The foamed preparations can for example by comminuted by milling and then filled into capsules.

EXAMPLES

After cooling, the foamed sample was milled for 30 s with an analytical mill (IKA A10). For the further experiments, the screened fraction which after milling was smaller than 250 μm was used.

The polymer foams produced were examined for crystallinity or amorphousness by means of XRD (X-ray diffractometry) and DSC (Differential Scanning calorimetry) using the following instruments and conditions:
XRD
Measuring instrument: Diffractometer D 8 Advance with 9-fold sample changer (Bruker/AXS)
Measurement type: θ-θ geometry in reflection
Angle range 2 Theta: 2-80°
Step width: 0.02°
Measurement time per angle step: 4.8 s
Divergence Slit: Göbel mirror with 0.4 mm orifice plate
Antiscattering Slit: collimator
Detector: Sol-X detector
Temperature: room temperature
Generator setting: 40 kV/50 mA
DSC
DSC Q 2000 from TA Instruments
Parameters:
Sample weighing: ca. 8.5 mg
Heating rate: 20 K/min The milled foams were filled into hard gelatin capsules. The active compound release was effected according to USP. apparatus (paddle method) 2, 37° C., 50 rpm (BTWS 600, Pharmatest) in 0.1 molar hydrochloric acid for 2 h. The detection of the active compound released was effected by UV spectroscopy (Lamda-2, Perkin Elmer). The samples taken were diluted with methanol directly after filtration, in order to prevent the poorly soluble active compound from crystallizing out.
Polymer 1

As polymer 1, a graft copolymer of polyethylene glycol 6000/N-vinylcaprolactam and vinyl acetate in the weight ratio 13/57/30 (Soluplus®, BASF) was used. The K value was 31-41, measured at 1 wt. % in ethanol. The glass transition temperature of the polymer was 75° C., determined by DSC. The polymer was in the form of a granulate.
Polymer 2

As polymer 2, a random copolymer of methacrylic acid/ethyl acrylate in a weight ratio of 1:1, having an average molecular weight Mw in the region of 250,000 D (available commercially as Kollicoat® MAE 100 P, BASF), was used. The polymer was in the form of a granulate.

Example 1

For the following Example 1, polymer 1 was used. 200 mg of polymer in the form of a sample pressed at 180° C. (diameter of 4.5 mm in a brass press mold for 5 minutes at 180° C. and a pressing force of 50 kN) were brought to the foam temperature stated below in a heatable vertical steel autoclave with an internal volume of 2.5 ml. At the upper end, this autoclave was equipped with a pressure sensor which measures the internal pressure at a rate of 1/ms. Pressure and temperature were continuously recorded via a computer.

Here it should be noted that the foam temperature was determined as the directly measured temperature of the bursting disk fitted at the underside of the autoclave, with the polymer lying on the bursting disk. By means of an automatic motor-driven pump (SITEC Model C), the stated propellant in the supercritical state was then pumped in and the relevant loading pressure applied. To compensate for temperature fluctuations, the pressure was readjusted within the first hour until a stable equilibrium state and a stable temperature of the bursting disk had been established.

In order to ensure sufficient time for the uptake of the propellant via diffusion processes, the sample was saturated for 22 h under constant conditions, even when an equilibrium state is already established after a shorter time.

For the foaming of the polymeric molding compound laden and heated according to embodiments of the invention, the pressure of the supercritical propellant in the chamber was then increased via the motor-driven pump over a period of a few seconds until attainment of the failure pressure of the bursting disk. The depressurization rate according to embodiments of the invention was then determined by evaluation of the pressure data of the sensor. In this, a linear pressure drop was assumed. The foaming experiment showed an almost complete pressure drop in the region of 2 ms, while the fall below the saturation pressure decisive for the cell nucleation took place even more rapidly.

After emergence from the pressure chamber through the hole forming in the bursting disk, the foamed sample was captured in a sponge and could be stably handled and examined directly after the foaming process.

The density of the foamed molded bodies was determined by calculation from the mass to volume ratio, while the cell parameters such as the average cell diameter were determined by evaluation of raster electron micrographs at 2 places at least in the foam. For the statistical evaluation, pictures with at least 10 whole cells in the picture detail were used.

| Polymer | Propellant | Saturation pressure [MPa] | Bursting disk temperature [° C.] | Saturation time [h] | Failure pressure [MPa] | Pressure drop rate [GPa/s] |
|---------|------------|---------------------------|----------------------------------|---------------------|------------------------|----------------------------|
| polymer 1 | $CO_2$ | 35.5 | 90 | 22 | 65.6 | 32 |

An optically homogeneous, open-cell, nanoporous foam with an average density of 200 kg/m³ and an average cell diameter of 150 nm was obtained.

Example 2

For the following Example 2, polymer 1 was also used. 30 g of polymer were previously mixed with 4.5 g of itraconazole (melting point of 166° C.) (corresponds to a loading of 15 wt. % based on the polymer mass) and melted in a high pressure capillary rheometer (Rheograph 2003) and extruded through a static mixer (Sulzer SMXS with a length of 18 mm) and a circular nozzle at a temperature of 150° C. by means of a plunger.

200 mg of the polymeric molding compound containing 15 wt. % itraconazole in the form of a sample pressed at 180° C. (diameter of 4.5 mm in a brass pressing mold for 5 minutes at 180° C. and a pressing force of 50 kN) and in turn dried for 20 h at 50° C. in the vacuum drying oven was brought to the foam temperature stated below in a specially prepared heatable vertical steel autoclave with an internal volume of 2.5 ml. At the upper end, this autoclave is equipped with a pressure sensor which measures the internal pressure at a rate of 1/ms. Pressure and temperature were continuously recorded via a computer, and could then be evaluated.

Here it should be noted that the foam temperature was determined as the directly measured temperature of the bursting disk located below, on which the polymer lay. By means of an automatic motor-driven pump (SITEC Model C), the stated propellant in the supercritical state was then pumped in and the relevant loading pressure applied. To compensate for temperature fluctuations, the pressure was readjusted within the first hour until a stable equilibrium state and a stable temperature of the bursting disk had been established.

In order to ensure sufficient time for the uptake of the propellant via diffusion processes, the sample was saturated for 22 h under constant conditions, even when an equilibrium state is already established after a shorter time.

For the foaming of the polymeric molding compound containing 15 wt. % itraconazole, laden and heated according to embodiments of the invention, the pressure of the supercritical propellant in the chamber was then increased via the motor-driven pump over a period of a few seconds until attainment of the failure pressure of the bursting disk. The depressurization rate according to embodiments of the invention was then determined by evaluation of the pressure data of the sensor. In this, a linear pressure drop was assumed. The foaming experiment showed an almost complete pressure drop in the region of 2 ms, while the fall below the saturation pressure decisive for the cell nucleation took place even more rapidly.

After emergence from the pressure chamber through the hole forming in the bursting disk, the foamed sample was captured in a sponge ca. 50 cm below the original position and could be stably handled and examined directly after the foaming process.

The density of the foamed molded bodies was determined by calculation from the mass to volume ratio, while the cell parameters such as the average cell diameter were determined by evaluation of raster electron micrographs at 2 places at least in the foam. For the statistical evaluation, pictures with at least 10 whole cells in the picture detail were used.

| Polymer | Propellant | Saturation pressure [MPa] | Bursting disk temperature [° C.] | Saturation time [h] | Failure pressure [MPa] | Pressure drop rate [GPa/s] |
|---------|------------|---------------------------|----------------------------------|---------------------|------------------------|----------------------------|
| Soluplus + 15 wt. % Itraconazole | $CO_2$ | 36.0 | 90 | 22 | 66.4 | 33 |

In this experiment, an optically homogeneous, open-cell, nanoporous foam with an average density of 220 kg/m³ and an average cell diameter of 140 nm was obtained.

Figure 1:
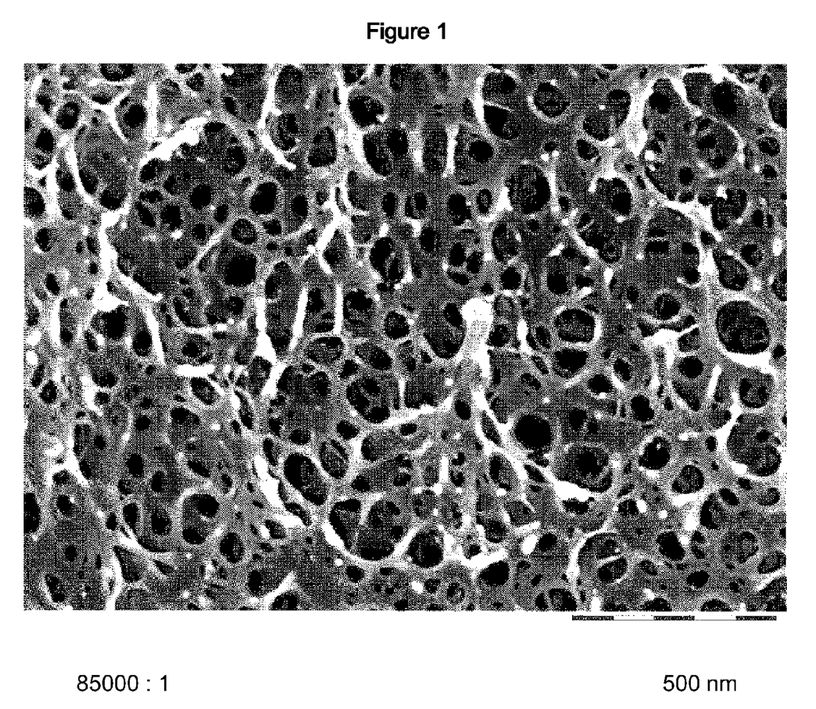
FIG. 1 is a scanning electron micrograph of a foamed preparation according to an embodiment of the invention.

In FIG. 1, a representative scanning electron micrograph of the foamed preparation is shown, from which the bicontinuous open-cell structure is evident.

The foamed sample was examined by XRD and by DSC and found to be amorphous.

Example 3

30 g of polymer 1 were premixed with 6 g of itraconazole (melting point 166° C.) (loading of 20 wt. %, based on the mass of polymer) and melted in a high pressure capillary rheometer (Rheograph 2003) and extruded in the same way as in Example 2.

In the same way as in Example 2, 200 mg of the polymeric molding compound were processed and foamed. Characterization took place as described in Example 2.

| Polymer | Propellant | Saturation pressure [MPa] | Bursting disk temperature [° C.] | Saturation time [h] | Failure pressure [MPa] | Pressure drop rate [GPa/s] |
|---------|------------|---------------------------|----------------------------------|---------------------|------------------------|----------------------------|
| Polymer 1 + 20 wt. % itraconazole | $CO_2$ | 35.4 | 86 | 22 | 65.7 | 32 |

An optically homogeneous, open-cell, nanoporous foam with an average density of 320 kg/m³ and an average cell diameter of 120 nm was obtained.

The foamed sample was examined by XRD and by DSC and found to be amorphous.

Example 4

30 g of polymer 1 were premixed with 6 g of fenofibrate (corresponding to a loading of 20 wt. %, based on the mass of polymer) and extruded in the same way as in Example 2.

In the same way as in Example 2, 200 mg of the fenofibrate-containing polymeric molding compound were processed and foamed. Characterization took place as described in Example 2.

| Polymer | Propellant | Saturation pressure [MPa] | Bursting disk temperature [° C.] | Saturation time [h] | Failure pressure [MPa] | Pressure drop rate [GPa/s] |
|---|---|---|---|---|---|---|
| Polymer 1 + 20 wt. % fenofibrate | $CO_2$ | 35.2 | 72 | 22 | 67.2 | 33 |

In this experiment according to embodiments of the invention, an optically homogeneous, open-cell, nanoporous foam with an average density of 320 kg/m³ and an average cell diameter of 130 nm was obtained.

The foamed sample was examined by XRD and by DSC and found to be amorphous.

Example 5

For the following Example 5, polymer 2 was used. 30 g of polymer were premixed with 6 g of itraconazole (corresponding to a loading of 20 wt. %, based on the mass of polymer) and extruded at a temperature of 180° C. in the same way as in Example 2.

In the same way as in Example 2, 200 mg of the polymeric molding compound containing 20 wt. % itraconazole, in the form of a sample pressed at 180° C. and dried in turn at 50° C. for 20 hours in a vacuum drying oven, were foamed and characterized.

| Polymer | Propellant | Saturation pressure [MPa] | Bursting disk temperature [° C.] | Saturation time [h] | Failure pressure [MPa] | Pressure drop rate [GPa/s] |
|---|---|---|---|---|---|---|
| Polymer 2 + 20 wt. % itraconazole | $CO_2$ | 35.2 | 116 | 22 | 43.1 | 22 |

In this experiment, an optically homogeneous, open-cell, nanoporous foam with an average density of 280 kg/m³ and an average cell diameter of 100 nm was obtained.

The foamed sample was examined by XRD and by DSC and found to be amorphous.

Figure 2:
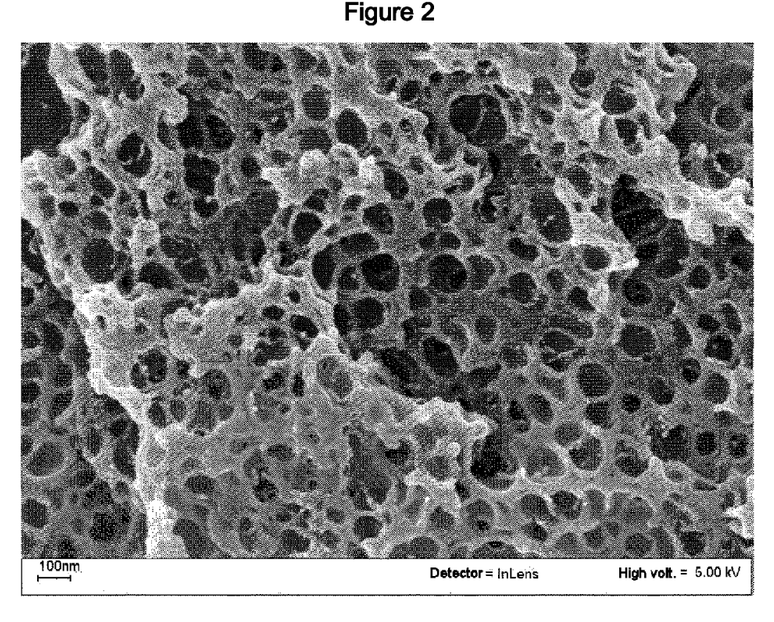
FIG. 2 is a scanning electron micrograph of a foamed preparation according to an embodiment of the invention.

FIG. 2 shows a representative scanning electron micrograph of the foamed preparation, from which the bicontinuous open-cell structure is evident.

Example 6

In this example, a solid foamed active ingredient preparation comprising the active ingredient homogeneously dispersed in the polymeric matrix was produced in a continuous extrusion process.

For the preparation of the polymeric molding compound, 200 kg of polymer 1 were precompounded at 180° C. in a standard twin-screw extruder with 20 wt. % itraconazole (based on the mass of polymer). The preparation laden with active ingredient was subsequently dried at 50° C. in a vacuum drying oven for 20 hours, and used in the subsequent foaming process.

In stage 1 of the foaming process, the polymeric molding compound laden with active ingredient was melted and homogenized in an extruder (Leistritz 18 mm) with a throughput of 2.5 kg/h. Immediately following the plastifying of the polymeric molding compound, supercritical $CO_2$ with a pressure in the region of 42 MPa was injected into the molding compound at a melt temperature of 160° C. For this purpose, a mass flow in the region of 0.800 kg/h $CO_2$ was set, giving a loading in the region of 32 wt. %, based on the mass of polymer and active ingredient (800 g/h $CO_2$/2500 g/h polymer+active ingredient).

The laden molding compound was then lowered to a temperature in the region of 50° C. ahead of the die, by means of mixing and cooling elements. The pressure along the process section after the injection of propellant was maintained, using melt pumps, above a minimum level of 35.0 MPa.

By extruding the laden molding compound under this pressure and with this total mass flow through a circular die with a diameter of 0.3 mm and length of 1.5 mm, it was possible to set a depressurization rate in the region of 320,000 MPa/s for the polymeric molding compound heated in accordance with the invention.

The product of this process according to embodiments of the invention was a continuously extruded, optically homogeneous, nanoporous foam with an average density of 380 kg/m³ and an average cell diameter of 270 nm.

The foamed sample was examined by XRD and by DSC and found to be amorphous.

Figure 3:
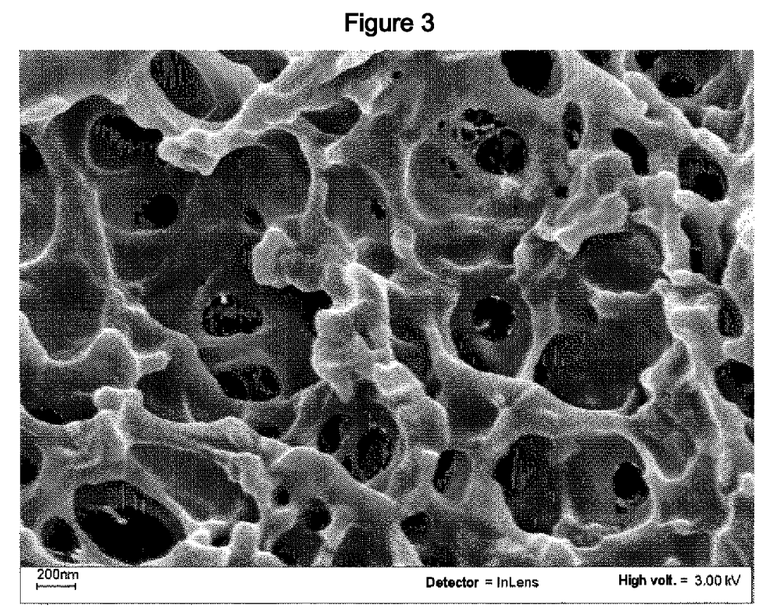
FIG. 3 is a scanning electron micrograph of a foamed preparation according to an embodiment of the invention.

FIG. 3 shows a representative scanning electron micrograph of the foamed preparation, from which the bicontinuous open-cell structure is evident.

The invention claimed is:

1. A process for the production of nanoporous foamed active substance-containing preparations, wherein the active substance is present in a pharmaceutically acceptable polymer, wherein:
   in stage a), loading of a polymeric molding compound or a polymer melt with a propellant is effected at a pressure above 10 MPa and at a temperature at which the propellant is in the supercritical state,
   in stage b), heating or cooling of the laden polymeric molding compound or melt is carried out under a pressure above 10 MPa to a temperature which lies in the range from −40 to +50° C. around the glass transition temperature of the polymeric molding compound prior to loading and
   in stage c), depressurization of the polymeric molding compound or melt laden in stage a) and heated or cooled under pressure in stage b) is effected with a depressurization rate in the range from 15,000 to 2,000,000 MPa/sec, wherein the temperature at the instant depressurization begins lies in the range from −40 to +50° C. around the glass transition temperature of the polymeric molding compound prior to loading and
   adding the active substance to the pharmaceutically acceptable polymer before melting, during stage b), or between stage b) and stage c).

2. The process of claim 1, wherein the loading and the heating or cooling of the polymeric molding compound or melt is performed under pressure in a pressure-resistant apparatus.

3. The process of claim 1, wherein the depressurization is effected via valves, pressure-limiting devices or by enlargement of the cavity of the pressure-resistant apparatus.

4. The process of claim 1, wherein the loading and the heating or cooling are performed continuously in an extruder and the depressurization is effected via a nozzle.

5. The process of claim 1, wherein an amorphous thermoplastic is used as the pharmaceutically acceptable polymer.

6. The process of claim 1, wherein a polymer selected from the group consisting of homo- and copolymers of N-vinyl-lactams is used as the polymer.

7. The process of claim 1, wherein the pressure lies in the range from 20 to 200 MPa in stage a) and in the range from 0.01 to 1 MPa (absolute) after the depressurization.

8. The process of claim 1, wherein carbon dioxide ($CO_2$) or dinitrogen oxide ($N_2O$) is used as the propellant.

9. The process of claim 1, wherein in stage b) heating or cooling to a temperature from −20 to +50° C. around the glass transition temperature is carried out.

10. The process of claim 1, wherein in stage b) heating or cooling to a temperature from 0 to +40° C. around the glass transition temperature is carried out.

11. The process of claim 1, wherein a polyether-containing graft copolymer is used as the pharmaceutically acceptable polymer.

12. The process of claim 11, wherein a polyether-containing graft copolymer, obtained by radical polymerization of i) 30 to 70 wt. % N-vinyllactam, ii) 15 to 35 wt. % vinyl acetate and ii) 10 to 35 wt. % of a polyether, is used as the pharmaceutically acceptable polymer.

13. The process of claim 1, wherein a copolymer of 50 wt. % methacrylic acid and 50 wt. % ethyl acrylate is used as the pharmaceutically acceptable polymer.

\* \* \* \* \*